United States Patent
Matsumoto

(10) Patent No.: US 8,927,285 B2
(45) Date of Patent: Jan. 6, 2015

(54) MICRO-ALGA BELONGING TO GENUS NAVICULA, PROCESS FOR PRODUCTION OF OIL BY CULTURE OF THE MICRO-ALGA, AND OIL COLLECTED FROM THE MICRO-ALGA

(75) Inventor: Mitsufumi Matsumoto, Kitakyusyu (JP)

(73) Assignee: Electric Power Development Co., Ltd., Tokyo (JP)

( * ) Notice: Subject to any disclaimer, the term of this patent is extended or adjusted under 35 U.S.C. 154(b) by 103 days.

(21) Appl. No.: 13/263,005

(22) PCT Filed: Mar. 10, 2010

(86) PCT No.: PCT/JP2010/001704
§ 371 (c)(1),
(2), (4) Date: Oct. 5, 2011

(87) PCT Pub. No.: WO2010/116611
PCT Pub. Date: Oct. 14, 2010

(65) Prior Publication Data
US 2012/0094339 A1    Apr. 19, 2012

(30) Foreign Application Priority Data

Apr. 10, 2009  (JP) ................. 2009-096362

(51) Int. Cl.
| | |
|---|---|
| C12N 5/04 | (2006.01) |
| C12P 7/64 | (2006.01) |
| C11B 1/10 | (2006.01) |
| C12N 1/12 | (2006.01) |
| C12P 5/00 | (2006.01) |
| C12P 5/02 | (2006.01) |
| C12R 1/89 | (2006.01) |

(52) U.S. Cl.
CPC . *C11B 1/10* (2013.01); *C11B 1/108* (2013.01); *C12N 1/12* (2013.01); *C12P 5/007* (2013.01); *C12P 5/02* (2013.01); *C12P 7/6463* (2013.01); *C12R 1/89* (2013.01); *Y02E 50/343* (2013.01)
USPC .......................................... 435/419; 435/134

(58) Field of Classification Search
None
See application file for complete search history.

(56) References Cited

U.S. PATENT DOCUMENTS

2008/0160593 A1    7/2008  Oyler

FOREIGN PATENT DOCUMENTS

| | | |
|---|---|---|
| JP | T-05-505726 | 8/1993 |
| JP | 09-065871 | 3/1997 |

(Continued)

OTHER PUBLICATIONS

Kitano et al., Enhanced eicosapentaenoic acid production by *Navicula* saprophila., Journal of Applied Phycologhgy, (1998), vol. 10, pp. 101-105.*

(Continued)

*Primary Examiner* — Alexander Kim
(74) *Attorney, Agent, or Firm* — Knobbe Martens Olson & Bear LLP

(57) ABSTRACT

Disclosed are: a microalga highly capable of producing aliphatic hydrocarbons of 16 to 26 carbon atoms; a process for producing oil, which comprises a step of culturing the microalga; oil collected from the microalga; a fuel produced from the microalga; and a method for fixing carbon dioxide, which comprises a step of culturing the microalga.
Specifically disclosed is a microalga belonging to the genus *Navicula*, which is capable of producing aliphatic hydrocarbons of 16 to 26 carbon atoms. More specifically disclosed is a microalga, *Navicula oiliticus* strain JPCC DA0580 (FERM BP-11201).

8 Claims, 3 Drawing Sheets

(56) References Cited

FOREIGN PATENT DOCUMENTS

| JP | A-09-234055 | 9/1997 |
|---|---|---|
| JP | T-2008-519129 | 6/2008 |
| WO | WO 2006/109588 | 10/2006 |
| WO | WO 2008/079724 A2 | 7/2008 |
| WO | WO 2008/134836 A2 | 11/2008 |
| WO | WO 2008/151149 | 12/2008 |
| WO | WO 2009/039201 A1 | 3/2009 |

OTHER PUBLICATIONS

Matsumoto et al., Marine Diatom, *Navicula* sp. Strain JPCC DA0580 and Marine Green Alga, *Chlorella* sp. Strain NKG400014 as Potential Sources for Biodiesel Production., Applied Biochemistry and Biotechnology (E pub Sep 9, 2009), vol. 161, Issue 1-8, pp. 483-490.*

Raja et al., "A Perspective on the Biotechnological Potential of Microalgae," Critical Reviews in Microbiology, vol. 34, pp. 77-88 (2008).

Belt et al., "Identification of a $C_{25}$ Highly Branched Isoprenoid Triene in the Freshwater Diatom *Navicula* Sclesvicensis," Organic Geochemistry, vol. 32, No. 9, pp. 1169-1172 (2001).

Damste et al., "Rapid Sulfurisation of Highly Branched Isoprenoid (HBI) Alkenes in Sulfidic Holocene Sediments from Ellis Fjord, Antarctica," Organic Geochemistry, vol. 38, No. 1, pp. 128-139 (2007).

Elloumi et al., "Detection of Water and Sediments Pollution of an Arid Saltern (Sfax, Tunisia) by Coupling the Distribution of Microorganisms With Hydrocarbons," Water Air Soil Pollut, vol. 187, No. 1-4, pp. 157-171 (2008).

Matsumoto, "J-Power Culture Collection kara no Ko Oil Sansei Kaiyo Bisai Sorui no Kensaku," Abstracts of the Annual Meeting of the Society for Biotechnology, Japan, vol. 61, p. 119, 11p12 (2009).

International Search Report issued in corresponding International Application No. PCT/JP2010/001704 mailed Jun. 1, 2010.

Supplementary European Search Report issued in European Patent Application No. 10761319.2 on Aug. 2, 2012.

Clark et al., "Distribution of *n*-Paraffins in Marine Organisms and Sediment," Limnology and Oceanography, vol. 12, pp. 79-87, 1967.

Sriharan et al., "Environmental Control of Lipids and Fatty Acid Production in the Diatom *Navicula*-Saprophila," Applied Biochemistry and Biotechnology, vol. 20/21, pp. 281-292, 1989.

Liang et al., "Total Lipid and Fatty Acid Composition of Eight Strains of Marine Diatoms," Chinese Journal of Oceanology and Limnology, vol. 18, No. 4, pp. 345-349, 2000.

Office Action mailed May 13, 2014 in counterpart Japanese Patent Application No. 2011-508201.

* cited by examiner

MICRO-ALGA BELONGING TO GENUS *NAVICULA*, PROCESS FOR PRODUCTION OF OIL BY CULTURE OF THE MICRO-ALGA, AND OIL COLLECTED FROM THE MICRO-ALGA

RELATED APPLICATIONS

This application is the U.S. National Phase filing under 35 U.S.C. §371 of PCT/JP2010/001704, filed Mar. 10, 2010, which designated the United States and was published in a language other than English, which claims priority under 35 U.S.C. §119(a)-(d) to Japanese Patent Application No. 2009-096362, filed Apr. 10, 2009. The contents of these applications are incorporated herein by reference in their entireties.

TECHNICAL FIELD

The present invention relates to: a microalga belonging to the genus *Navicula*; a process for producing oil, which comprises a step of culturing the microalga; and oil collected from the microalga. More specifically, the present invention relates to: a microalga belonging to the genus *Navicula*, which is capable of producing aliphatic hydrocarbons of 16 to 26 carbon atoms; a process for producing oil, which comprises a step of culturing the microalga; oil collected from the microalga; a dried algal biomass produced by drying the microalga; a fuel produced from the microalga; and a method for fixing carbon dioxide, which comprises a step of culturing the microalga.

BACKGROUND ART

There have been several reported methods for producing heavy oil-based or light oil-based hydrocarbons, so-called biofuels, through the culture of microalgae.

Regarding algae capable of producing heavy oil-based hydrocarbons: a microalga, *Botryococcus braunii*, which is capable of producing a hydrocarbon of 36 carbon atoms (refer to Non-patent Document 1); and a microalga, *Botryococcus braunii* race A, which is capable of producing a hydrocarbon of 33 carbon atoms (refer to Patent Document 1); have been known.

Moreover, regarding algae capable of producing light oil-based hydrocarbons: microalgae, *Nostoc muscorum, Trichodesmium erythaeum, Plectonema terebrans*, and the like, which are capable of producing a hydrocarbon of 17 carbon atoms (refer to Non-patent Document 1); a microalga, *Coccochloris elabens*, and the like, which are capable of producing a hydrocarbon of 19 carbon atoms (refer to Non-patent Document 1); a microalga *Pseudochoricystis ellipsoidea* strain MBIC11204, which is capable of producing hydrocarbons of 17, 18, 19, and 20 carbon atoms (refer to Patent Document 2); and a microalga, *Choricystis minor* stain SAG17.98, which is capable of producing hydrocarbons of 17, 19, 21, and 23 carbon atoms (refer to Patent Document 2); have been known.

Light oil-based hydrocarbons that can be produced by microalgae are industrially useful as a diesel fuel, and also show promise as a carbon neutral fuel intended for the prevention against global warming.

However, the content percent of light oil-based hydrocarbons in the dried algal biomass produced by drying the microalgae is usually about 0.025 to 0.12% by mass (refer to Non-patent Document 1), meaning that the hydrocarbon productivity thereof is not always sufficient.

REFERENCES

Patent Document

Patent Document 1: Japanese Unexamined Patent Application, First Publication No. H09-234055
Patent Document 2: PCT International Publication No. WO 2006/109588, Pamphlet Non-Patent Document Non-patent Document 1: R. Raja, S. Hemaiswarya, N. Ashok Kumar, S. Sridhar and R. Rengasamy (2008), A Perspective on the Biotechnological Potential of Microalgae. Critical Reviews in Microbiology, 34: 77-88.

DISCLOSURE OF INVENTION

The present invention was completed with consideration of the above-mentioned situation. It is an object to provide: a microalga highly capable of producing aliphatic hydrocarbons of 16 to 26 carbon atoms; a process for producing oil, which comprises a step of culturing the microalga; oil collected from the microalga; a dried algal biomass produced by drying the microalga; a fuel produced from the microalga; and a method for fixing carbon dioxide, which comprises a step of culturing the microalga.

In order to achieve the above-mentioned object, the present invention adopts the following constitutions.

(1) A microalga belonging to the genus *Navicula*, which is capable of producing aliphatic hydrocarbons of 16 to 26 carbon atoms.

(2) A microalga, *Navicula oiliticus*, which is capable of producing aliphatic hydrocarbons of 16 to 26 carbon atoms.

(3) A microalga, *Navicula oiliticus* strain JPCC DA0580 (FERM BP-11201).

(4) A process for producing oil, comprising: a step of culturing the microalga according to any one of (1) to (3) mentioned above.

(5) A process for producing oil according to (4) mentioned above, further comprising, after the culturing step: a step of additionally culturing the microalga with a different medium having lower concentration(s) of nutrient salt(s) as compared to the medium that has been used for the preceding culture.

(6) A process for producing oil according to either one of (4) and (5) mentioned above, wherein the oil includes a neutral lipid.

(7) A process for producing oil according to any one of (4) to (6) mentioned above, wherein the oil includes squalene.

(8) A process for producing oil according to any one of (4) to (7) mentioned above, further comprising, after the culturing step: a step of extracting oil from the culture product by using an organic solvent, the organic solvent being any one of solvents selected from a solvent comprising n-hexane, a solvent comprising n-hexane and methanol, and a solvent comprising n-hexane and ethanol.

(9) Oil produced by the process for producing oil according to any one of (4) to (8) mentioned above.

(10) A dried algal biomass produced by drying the microalga according to any one of (1) to (3) mentioned above.

(11) A fuel produced from the microalga according to any one of (1) to (3) mentioned above.

(12) A method for fixing carbon dioxide, comprising: a step of culturing the microalga according to any one of (1) to (3) mentioned above.

Note that, in the claims and the description of this application, the phrase "capable of producing aliphatic hydrocarbons of 16 to 26 carbon atoms" means to have an ability to produce aliphatic hydrocarbons mainly of 16, 18, 20, 22, 24, and 26 carbon atoms. Moreover, the term "oil" refers to a liquid component mainly consisting of hydrophobic organic compounds. The hydrophobic organic compounds can be exemplified by aliphatic hydrocarbons, neutral lipids, and the like.

The present invention is able to provide; a microalga highly capable of producing aliphatic hydrocarbons of 16 to 26 carbon atoms; a process for producing oil, which comprises a step of culturing the microalga; oil collected from the microalga; a dried algal biomass produced by drying the microalga; a fuel produced from the microalga; and a method for fixing carbon dioxide, which comprises a step of culturing the microalga.

BEST MODE FOR CARRYING OUT THE INVENTION

Figure 1:
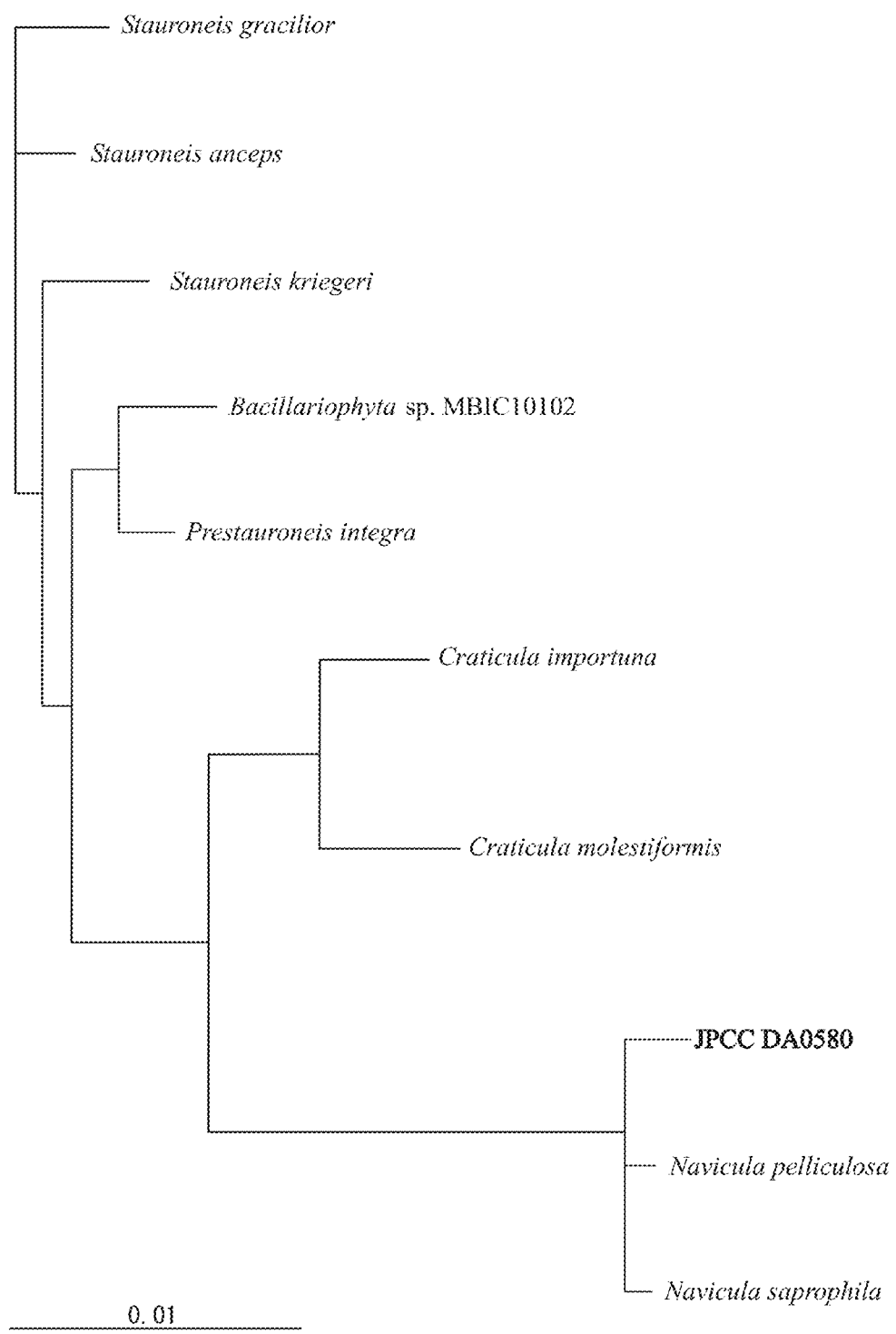
FIG. 1 shows a molecular phylogenic tree made by using the 18S rDNA nucleotide sequence of the strain JPCC DA0580.

Hereunder is a detailed explanation of the present invention.

<Microalgae Belonging to the Genus *Navicula*>

The microalgae belonging to the genus *Navicula* of the present invention are capable of producing aliphatic hydrocarbons of 16 to 26 carbon atoms. Here, the term "aliphatic hydrocarbons of 16 to 26 carbon atoms" refers to aliphatic hydrocarbons mainly of 16, 18, 20, 22, 24, and 26 carbon atoms.

As the above-mentioned microalga, particularly preferred is a microalga, *Navicula oiliticus*, because it has a high content percent of aliphatic hydrocarbons of 16 to 26 carbon atoms in the algal biomass, and also it can be readily cultured. More preferred is a microalga, *Navicula oiliticus* strain JPCC DA0580 (FERM BP-11201) (hereunder, abbreviated as "strain JPCC DA0580").

The strain JPCC DA0580 is more preferred for use as the microalga of the present invention because it is highly capable of producing neutral lipids and squalene, as well as being capable of producing aliphatic hydrocarbons of 16 to 26 carbon atoms as mentioned above. The neutral lipids will be explained later.

The strain JPCC DA0580 is a novel strain of new marine microalgal species belonging to the division Chromophyta, class Bacillariophyceae, order Pennales, suborder Raphidineae, family Naviculaceae, isolated from seawater in a brackish-water area by the inventor of the present invention.

Hereunder is an explanation of the method for isolating the microalga and the situation regarding how the microalgal strain JPCC DA0580 was determined to be a novel strain of new species.

(Medium Preparation Method)

A liquid medium in which 75.0 mg/l of sodium nitrate, 5.0 mg/l of disodium hydrogen phosphate, 30.0 mg/l of sodium metasilicate nonahydrate, 1.0 ml of an f/2 trace metal solution, 0.5 ml of an f/2 vitamin solution, and 37 g/l of artificial seawater (Product Name: Marine Art SF-1, manufactured by Senju Pharmaceutical Co., Ltd.) had been dissolved at the predetermined concentrations in distilled water, was prepared as an f/2 medium.

The f/2 trace metal solution was prepared as an aqueous solution having the composition of: 4.36 g/l of $Na_2$ EDTA dihydrate, 3.15 g/l of ferric chloride hexahydrate, 180 mg/l of manganese (II) chloride tetrahydrate, 22.0 mg/l of zinc sulfate heptahydrate, 10.0 mg/l of cobalt (II) chloride hexahydrate, 6.3 mg/l of sodium molybdate (VI) dihydrate, and 9.8 mg/l of copper (II) sulfate pentahydrate.

The f/2 vitamin solution was prepared as an aqueous solution having the composition of: 200.0 mg/l of thiamine, 0.1 mg/l of biotin, and 1.0 mg/l of vitamin $B_{12}$.

Moreover, an f/2 agar medium was prepared by adding agar to the f/2 medium composition at a concentration of 1.2% (w/v).

The artificial seawater is a mixture of salts that simulates salts contained in natural seawater. An aqueous solution having the seawater component that simulates natural seawater can be produced by dissolving a predetermined amount (37 g/l) of the artificial seawater in distilled water.

(Isolation Method)

To a 24-well microtiter plate containing 2 ml of the f/2 medium was added an appropriate amount of a silt sample collected from a mangrove forest in the junction of Sumiyo River and Yakugachi River, Amami-shi, Kagoshima Prefecture, Japan, on July, 2005. The plate was then subjected to static culture under 1000 lux (1×) illumination, and a part of the culture solution in the well where the growth of a microalga was observed was taken out. The thus taken culture solution was inoculated onto the f/2 agar medium, and incubated under the same illumination condition. By so doing, the unicellular algal strain JPCC DA0580 was obtained in the form of brown unialgal (isolated) colonies.

(Morphological Characteristics)

As a result of the seven days culture at 25° C. on the agar medium, brown colonies of the strain JPCC DA0580 having their diameters of about 2.0 to 5.0 mm were obtained. These colonies were punctiform and semi-lenticular with no elevation. The periphery was complete, and the surface was smooth. Moreover, neither morphological alteration of colony due to mutation, nor morphological alteration of colony due to the culture condition or the physiological condition, was found.

The marine microalga was unicellular in the colonies with an average size of about 10 to 20 μm, and sometimes formed colony groups. The vegetative cell had a rhombic cell shape with neither instillation nor contractile vacuole. No planktonic property was found. The lorica was vitreous with a raphe, and the cell surface was smooth. The vegetative cell was not flagellate with no motility.

Figure 4:
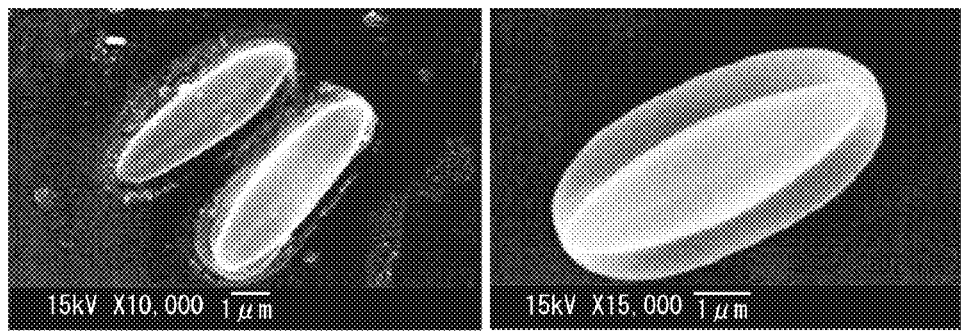
FIG. 4 shows electron microscopy images of *Navicula oiliticus* strain JPCC DA0580 (FERM BP-11201) (Left: magnification ×10,000, Right: magnification ×15,000).

The electron microscopy images of the strain JPCC DA0580 are shown in FIG. 4.

(Reproductive Behavior)

The strain JPCC DA0580 reproduces both sexually and asexually. In the asexual reproduction, the proliferation takes place asexually through binary division. The cell division proceeds inside the lorica. Two daughter cells form new semi-loricae respectively inside the outer shell and the inner shell of the parent cell. The semi-loricae of the parent cell are respectively given to the daughter cells one by one. As a result, one of the daughter cells has the same size (of the lorica) as that of the parent cell, while the other one uses the inner shell of the parent cell as its outer shell. As a result, the other daughter cell is one size smaller than the parent cell. When its size becomes small to some degree, sexual reproduction takes place. This cell undergoes meiotic division to create homogametes. Resultant zygotes approach each other through their loricae and join each other by altering their protoplasts into amoeba-like forms. By so doing, an auxospore is produced. This grows to expand its volume back to a reasonable size as a normal cell. Such a reproduction behavior is adopted.

(Physiological/Biochemical Properties)

Culture solution: Grows in a seawater-based culture solution. Not growable in freshwater.

Photosynthesis: Able to grow photoautotrophically through photosynthesis. Heterotrophic growth is not observed.

Contained pigments: Chlorophylls a, c1, and c2, and Carotenoid pigments mainly consisting of fucoxanthin and fucoxanthin derivatives Reserve substance: Starch Growth temperature: 20° C. to 35° C. (optimum temperature: 25° C.)

Growth pH: 7.0 to 9.0 (optimum pH: 8.0)

Intracellular accumulation of abundance of oil including aliphatic hydrocarbons of 16 to 26 carbon atoms, neutral lipids, and squalene, which can be stained with Nile red.

Growth period: One week (the growth period means a period of time necessary for the turbidity (OD750) to reach 0.05 to 1.2)

Figure 5:
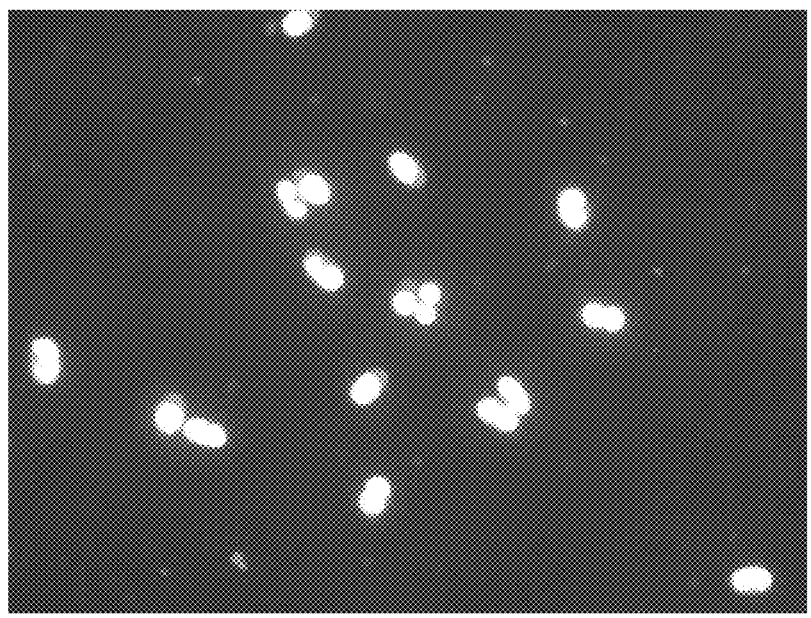
FIG. 5 shows a fluorescence microscopy image of *Navicula oiliticus* strain JPCC DA0580 (FERM BP-11201) stained with Nile red (Bright areas with fluorescent emission: oil in the algal biomass visualized by Nile red, Dim areas: photosynthetic pigments and the like visualized by autofluorescence).

As shown in FIG. 5, the observation of the Nile red-stained strain JPCC DA0580 under fluorescence microscopy confirms the presence of oil visualized by Nile red as indicated by the areas with bright fluorescent emission within the algal biomass in the fluorescence visual field. The oil can be intracellularly accumulated in the form of oil droplets in the algal biomass. In addition, the oil includes aliphatic hydrocarbons of 16 to 26 carbon atoms, neutral lipids, and squalene.

From the above-mentioned points of the morphological characteristics, the reproductive behavior, and the physiological/biochemical properties, it was suggested that the strain JPCC DA0580 was an alga belonging to the division Chromophyta, class Bacillariophyceae, order Pennales, suborder Raphidineae, family Naviculaceae. In addition, the nucleotide sequence of the 18S rDNA region was determined by conducting DNA extraction from the strain JPCC DA0580, PCR amplification of the 18S rDNA region thereof, and subsequent sequence analysis with use of the DNA extraction kit (Product Name: QIAamp DNA Blood Mini Kit 50, manufactured by QIAGEN) according to a conventionally known method. The thus obtained 18S rDNA nucleotide sequence is shown in SEQ ID NO:1 of the sequence listing. The obtained 18S rDNA nucleotide sequence was then subjected to homology search (Blast search) by cross-checking with the public database, DNA Data Bank of Japan (DDBJ), and phylogenetic analysis with use of the Clustal W alignment software and the Treeview display software. The resulting phylogenetic diagram is shown in FIG. 1.

The isolated strain JPCC DA0580 was classified into the family Naviculaceae in the above-mentioned phylogenetic tree, and formed a cluster with diatoms belonging to the genus *Navicula*. However, since a branch separating from genetically identified known species of the genus *Navicula* was confirmed, it was determined that the strain JPCC DA0580 isolated by the inventor of the present invention was a new algal species of the genus *Navicula*. Therefore, the strain was given the nomenclature of *Navicula oiliticus* strain JPCC DA0580.

The strain JPCC DA0580 was deposited with International Patent Organism Depositary, National Institute of Advanced Industrial Science and Technology (Tsukuba Central 6, 1-1-1 Higashi, Tsukuba-shi, Ibaraki-ken #305-8566, Japan) as of Mar. 16, 2009 with the accession number of FERM BP-11201 (transferred from the national accession number of FERM P-21788 deposited as of Mar. 16, 2009).

The strain JPCC DA0580 was deposited with the International Patent Organism Depositary, National Institute of Advanced Industrial Science and Technology on Dec. 4, 2009 with the accession number of FERM BP-11201. The depositis located at AIST Tsukuba Central 6, 1-1, Higashi 1-chome Tsukuba-shi, Ibaraki-ken 305-8566, Japan. The AIST deposit was accompanied by documents describing scientific characteristics and taxonomic position and thus meets all of the requirements of the Budapest treaty. The specific biological materials will be irrevocable and without restriction or condition released to the public upon the issuance of patent.

Moreover, the oil does not only include the aliphatic hydrocarbons of 16 to 26 carbon atoms, the neutral lipids, and the squalene, but can also contain aliphatic hydrocarbons of 27 or more carbon atoms, phospholipids, free fatty acids, steroidal compounds, photosynthetic pigments such as carotenoids including fucoxanthin and fucoxanthin derivatives, and the like.

The term "aliphatic hydrocarbons of 16 to 26 carbon atoms" refers to aliphatic hydrocarbons mainly of 16, 18, 20, 22, 24, and 26 carbon atoms, and in more detail, linear aliphatic saturated hydrocarbons mainly of 16, 18, 20, 22, 24, and 26 carbon atoms.

As will be explained later, the term "neutral lipids" refers to neutral lipids mainly having a tetradecanoyl group (myristoyl group), a hexadecanoyl group (palmitoyl group), a hexadecenoyl group (palmitoleoyl group), an octadecenoyl group (oleoyl group), and an eicosapentaenoyl group, as the acyl groups, the majority of which are triglycerides having these acyl groups.

The term "squalene" refers to 2,6,10,15,19,23-hexamethyltetracosa-2,6,10,14,18,22-hexaene.

The term "aliphatic hydrocarbons of 27 or more carbon atoms" refers to aliphatic hydrocarbons other than squalene.

If n-hexane is used as a solvent to extract oil from the strain JPCC DA0580, usually the aforementioned types of neutral lipids such as triglycerides account for about 80% by mass of the extracted oil, meaning that these neutral lipids can reach 36% by mass or more of the dried algal biomass of the strain JPCC DA0580. Note that, these values are calculated based on the assumption that the aforementioned types of triglycerides are oleic acid triglycerides.

Moreover, the amounts of the aliphatic hydrocarbons of 16 to 26 carbon atoms, and the squalene, contained in the extracted oil, can reach respectively 0.2% by mass or more, and 0.3% by mass or more of the dried algal biomass of the strain JPCC DA0580.

Note that, the composition of the extracted oil shows usual values obtained by the culture of the strain JPCC DA0580 with the f/2 medium in accordance with the aeration culture method that will be explained later. If the method of culturing the microalga is changed, the composition of the extracted oil may be different.

The majority of the fatty acids constituting the aforementioned types of neutral lipids such as triglycerides are tetradecanoic acid (myristic acid having 14 carbon atoms with no double bond), hexadecanoic acid (palmitic acid having 16 carbon atoms with no double bond), hexadecenoic acid (palmitoleic acid having 16 carbon atoms with one double bond), octadecenoic acid (oleic acid having 18 carbon atoms with one double bond), and eicosapentaenoic acid (EPA having 20 carbon atoms with five double bonds). The contents of these fatty acids constituting the aforementioned types of neutral lipids such as triglycerides in the dried algal biomass of the strain JPCC DA0580 are, in the order of the fatty acids as set forth, about 1.0% by mass, about 12.7% by mass, about 17.0% by mass, about 0.8% by mass, and about 1.4% by mass. In other words, the fatty acids constituting the aforementioned types of neutral lipids such as triglycerides account for about 32.9% by mass of the dried algal biomass.

Note that, the content percents of the fatty acids constituting the aforementioned types of neutral lipids such as triglycerides in the dried algal biomass mean proportions by mass of fatty acid methyl esters, which are methyl esterification products of these fatty acids, in the dried algal biomass.

<Process for Producing Oil>

The process for producing oil of the present invention comprises a step of culturing the above-mentioned microalga belonging to the genus *Navicula* according to the present invention. The oil can be produced by culturing the microalga according to the present invention, recovering the microalga grown by the culturing step from the medium, and collecting the oil contained in the thus obtained microalga.

As the microalga belonging to the genus *Navicula*, particularly preferred is a microalga, *Navicula oiliticus*, because it has a high content percent of aliphatic hydrocarbons of 16 to 26 carbon atoms in the algal biomass, and also it can be readily cultured. More preferred is the strain JPCC DA0580.

The strain JPCC DA0580 is more preferred for use as the microalga of the present invention because it is highly capable of producing neutral lipids and squalene, as well as being capable of producing aliphatic hydrocarbons of 16 to 26 carbon atoms.

Regarding the step of culturing the microalga, it is possible to apply a known method capable of culturing microalgae belonging to the genus *Navicula*. For example, this step can be achieved by inoculating the microalga to a liquid medium in a culture vessel such as a flat-shaped flask, and subjecting it to an aeration culture under illumination with mild shaking to a degree enough to avoid sedimentation of the algal biomass.

The liquid medium is not specifically limited as long as the liquid medium is capable of culturing the microalga, and it is possible to use a known medium. A preferred example thereof can be given by the above-mentioned f/2 medium that had been used for the isolation of the strain JPCC DA0580, because the microalga can grow well therewith.

The concentration of the artificial seawater (Product Name: Marine Art SF-1, manufactured by Senju Pharmaceutical Co., Ltd.) in the liquid medium is preferably from 30 to 100% (w/v), more preferably from 50 to 100% (w/v), yet more preferably from 70 to 100% (w/v), particularly preferably from 90 to 100 (w/v), and most preferably from 95 to 100% (w/v), provided that the dose of 37 g/l is defined as 100% (w/v). Here, an aqueous solution produced by dissolving the predetermined amount (37 g/l) of the artificial seawater in distilled water is deemed to have substantially equivalent salt concentration to that of natural seawater.

The illumination condition can be appropriately adjusted depending on the algal biomass concentration in the culture solution. For example, it is preferably 500 1x or higher, more preferably from 1000 to 30000 1x, yet more preferably from 1000 to 10000 1x, particularly preferably from 1000 to 6000 1x, and most preferably from 1000 to 3000 1x.

Regarding the aeration gas in the aeration culture, it is possible to use a known aeration gas suitable for the growth of the microalga. For example, it is possible to use normal air, air with $CO_2$ addition, and the like. Of these, preferred is air with $CO_2$ addition because the microalga can grow better and the growth period can be shortened.

The $CO_2$ concentration in the air with $CO_2$ addition is preferably from 0.05 to 10% (v/v), more preferably from 0.05 to 5.0% (v/v), and most preferably from 1.0 to 3.0% (v/v).

Regarding the aeration rate in the aeration culture, it is possible to apply a known aeration rate suitable for the growth of the microalga. For example, it is preferably from 0.5 to 5 vvm, more preferably from 0.5 to 3.0 vvm, and yet more preferably from 0.5 to 2.0 vvm.

The incubation temperature in the aeration culture may be a known incubation temperature suitable for the growth of the microalga. It is usually preferable to carry it out at 20 to 35° C., and more preferably at 25 to 30° C.

Regarding the period of the aeration culture, it is possible to continue the culture as long as the microalga can grow. It is usually preferable to carry it out for one to four weeks, more preferably for one to three weeks, and yet more preferably for one to two weeks.

In the process for producing oil of the present invention, it is also possible to additionally culture the microalga under nutrient restriction, after the period of the aeration culture. The content percent of oil in the algal biomass (weight percent of oil in the dried algal biomass) can be increased by culturing under such nutrient restriction. Accordingly, it is possible to increase the content percent of oil in the algal biomass by growing the microalga with a medium under no nutrient restriction (nutrient medium) during the period of the aeration culture, and on the completion of the culture up to a predetermined amount, shifting it to the culture under nutrient restriction. By so doing, the oil producibility can be improved.

Here, the above-mentioned term "culture under nutrient restriction" refers to culture with a medium having smaller amounts of vitamin-including nutrient salts than usual (nutrient restriction medium). For example, assuming that the content of the vitamin-including nutrient salts (sodium nitrate, disodium hydrogen phosphate, sodium metasilicate, the f/2 trace metal solution, and the f/2 vitamin solution) in the above-mentioned f/2 medium (nutrient liquid medium) that has been used for the isolation of the strain JPCC DA0580, is 100%, then culture with a f/2 medium having a lower content of these salts below 100% (nutrient restriction liquid medium) meets the criteria of the term "culture under nutrient restriction".

The content of the vitamin-including nutrient salts in the nutrient restriction liquid medium is preferably from 0 to 60%, more preferably from 0 to 30%, yet more preferably from 0 to 20%, particularly preferably from 0 to 10%, and most preferably 0%, so as to increase the content percent of oil in the microalga.

The method of shifting from the nutrient liquid medium to the nutrient restriction liquid medium as mentioned above, is not specifically limited, and it is possible to shift to the nutrient restriction medium either at once or gradually. The method of shifting at once can be exemplified by a method in which the algal biomass is precipitated by centrifugation, then the nutrient liquid medium in the form of supernatant is removed, and thereafter the nutrient restriction liquid medium is charged. Moreover, the method of shifting gradually can be exemplified by a method in which a nutrient liquid medium including the algal biomass is charged in one side, out of two areas partitioned by a semipermeable membrane, and a nutrient restriction liquid medium is charged in the other side so as to utilize the principle of osmotic pressure to gradually lower the content concentration of the vitamin-including nutrient salts in the liquid medium including the algal biomass, thereby making it into a nutrient restriction liquid medium.

The period of the culture under nutrient restriction is not specifically limited as long as the effect of the present invention is not impaired. The period may be optional as long as the content percent of oil in the microalga can increase during the period. The period is preferably from 3 to 20 days, more preferably from 3 to 10 days, and yet more preferably from 3 to 7 days.

The method of recovering the cultured microalga can be conducted by a known method, which can be exemplified by: a method in which the algal biomass is precipitated by centrifuging the culture solution, and then recovered as a pellet; a method in which the culture solution is passed through a filter with pores which do not allow the passage of the microalga, and the algal biomass remaining on the filter is recovered; or the like.

The method of collecting oil contained in the algal biomass yielded by the above-mentioned culture method and recovery method is not specifically limited as long as the effect of the present invention is not impaired. For example, the oil contained in the algal biomass can be extracted into an organic solvent by suspending the recovered algal biomass into the organic solvent.

The organic solvent is not specifically limited as long as the effect of the present invention is not impaired, and as long as the oil contained in the algal biomass can be dissolved therein. The organic solvent can be exemplified by n-hexane (hereunder, referred to as hexane), acetone, acetonitrile, methanol, ethanol, butanol, chloroform, and the like. Of these, hexane is preferred in terms of the oil extraction efficiency. In addition, it is either possible to use a single type alone, or a combination of two or more types, of these organic solvents.

Moreover, in order to improve the oil extraction efficiency, it is preferable to physically disrupt the algal biomass by subjecting the organic solvent suspended with the algal biomass to an ultrasonic homogenizer, or the like.

The hexane that has been exemplified as a preferred solvent to extract oil from the algal biomass of the microalga, can be used either as a monophasic solvent by itself, or as a biphasic solvent mixed with methanol and/or ethanol.

In the case of using a biphasic solvent mixed with methanol, it is preferable to have the mixture at a ratio (by volume) of hexane:methanol=10:0 to 5:5, more preferably a ratio of hexane:methanol=10:0.5 to 8:2, and yet more preferably a ratio of hexane:methanol=10:1 to 9:1.

In the case of using a biphasic solvent mixed with ethanol, it is preferable to have the mixture at a ratio (by volume) of hexane:ethanol=10:0 to 5:5, more preferably a ratio of hexane:ethanol=10:0.5 to 8:2, and yet more preferably a ratio of hexane:ethanol=10:1 to 9:1.

In the case of using a biphasic solvent as a mixture of hexane with ethanol and methanol, ethanol and methanol are mixed at an optional ratio (by volume) for use as a monophasic solvent. In this case, it is preferable to have the mixture at a ratio (by volume) of hexane:ethanol+methanol=10:0 to 5:5, more preferably hexane:ethanol+methanol=10:0.5 to 8:2, and yet more preferably hexane:ethanol+methanol=10:1 to 9:1.

It is more preferable to use ethanol rather than methanol so as to improve the safety of the solvent and to increase the oil extraction yield.

For the extraction of oil from the algal biomass by using an organic solvent, it is possible to conduct the oil extraction with the organic solvent after the algal biomass has been dried, or to conduct the oil extraction with the organic solvent while the algal biomass is in an undried state containing moisture.

For the extraction of oil from the algal biomass of the microalga according to the present invention by using an organic solvent, it is preferable to conduct the oil extraction with the organic solvent from the algal biomass in an undried state, rather than previously drying the algal biomass, because the oil extraction yield can be increased.

For the extraction of oil from the algal biomass of a known microalga by using an organic solvent, it is usual that the oil extraction yield can be increased by previously drying the algal biomass, and then conducting the oil extraction with the organic solvent from the algal biomass in a dried state. However, it is unfavorable to previously dry the algal biomass when it comes to time and energy cost required for the drying treatment. In this point, the algal biomass of the microalga according to the present invention can have a very favorable property that enables efficient oil extraction from the algal biomass in an undried state. This advantage makes it possible to achieve an energy reduction in the production process of a biofuel or the like with use of the microalga of the present invention.

For the extraction of oil from the algal biomass in an undried state by using an organic solvent, the use of a biphasic solvent consisting of hexane with methanol and/or ethanol can increase the extraction yield. Regarding this biphasic solvent, particularly preferred is a biphasic solvent having the mixture at a ratio (by volume) of hexane:methanol=10:1, or a biphasic solvent having the mixture at a ratio (by volume) of hexane:ethanol=10:1.

For the extraction of oil from the algal biomass in a dried state by using an organic solvent, the use of a hexane monophasic solvent can improve the extraction efficiency.

Since such an organic solvent has a lower boiling point than that of the above-mentioned oil, the solvent can be removed by blowing a nitrogen gas stream, reducing the pressure, or such a means. Recycling of the solvent is also possible.

In addition, the oil extracted by the organic solvent can be further refined, if necessary. This refining method can be carried out by a known method, which is exemplified by preparative isolation of each component contained in the oil by means of solid-phase extraction using a silica gel, liquid chromatography, distillation, or the like.

The oil produced by the process for producing oil of the present invention includes a type of oil that becomes observable by staining the microalga with Nile red. This oil includes aliphatic hydrocarbons of 16 to 26 carbon atoms. The term "aliphatic hydrocarbons of 16 to 26 carbon atoms" refers to aliphatic hydrocarbons mainly of 16, 18, 20, 22, 24, and 26 carbon atoms.

In addition, the oil does not only include the aliphatic hydrocarbons of 16 to 26 carbon atoms, but can also contain neutral lipids, squalene, aliphatic hydrocarbons of 27 or more carbon atoms, phospholipids, free fatty acids, steroidal compounds, photosynthetic pigments such as carotenoids, and the like.

When the strain JPCC DA0580 is used as the microalga for the process for producing oil of the present invention, the explanation of the thus produced oil is the same as the above-mentioned explanation of the oil that can be accumulated in the algal biomass of the strain JPCC DA0580.

<Oil>

The oil of the present invention is produced by the process for producing oil according to the present invention.

The explanation of this oil is the same as the above-mentioned explanation of the oil in the process for producing oil.

In addition, it is possible to refine the aliphatic hydrocarbons of 16 to 26 carbon atoms from the oil. Furthermore, if the oil includes neutral lipids and/or squalene, it is also possible to refine the neutral lipids and/or squalene from the oil.

This refining method is not specifically limited and can be carried out by a known method. For example, the refining can be achieved by dissolving the hexane-extracted oil from the microalga in an organic solvent such as hexane, and then charging a silica gel in this solution to adsorb other substances than the aliphatic hydrocarbons so as to elute out these aliphatic hydrocarbons by themselves. Moreover, the refining can also be achieved by adsorbing the neutral lipids to a silica gel, and then eluting them out with use of an organic solvent or the like. Furthermore, the eluted aliphatic hydrocarbons of 16 to 26 carbon atoms can be separated from the squalene by applying a known refining method such as distillation or chromatography to the aliphatic hydrocarbons.

The organic solvent for dissolving the oil can be exemplified by the same organic solvents that have been exemplified in the above-mentioned explanation of the process for producing oil.

<Dried Algal Biomass>

The dried algal biomass of the present invention is a dried matter of the microalga belonging to the genus *Navicula* according to the present invention.

The microalga can be exemplified by the same microalgae that have been exemplified in the above-mentioned explanation of the microalga belonging to the genus *Navicula* according to the present invention.

The method of drying the microalga is not specifically limited as long as it is capable of removing the moisture in the algal biomass. The method can be exemplified by a method of drying the algal biomass with sun, a method of blowing dry air to the algal biomass, a method of lyophilizing (freeze-drying) the algal biomass, or the like. Of these, a drying method by means of lyophilization is preferred since the components contained in the algal biomass can be kept from degrading.

<Fuel>

The fuel of the present invention is produced from the microalga belonging to the genus *Navicula* according to the present invention.

The microalga can be exemplified by the same microalgae that have been exemplified in the above-mentioned explanation of the microalga belonging to the genus *Navicula* according to the present invention.

The method of utilizing the microalga as a fuel can be exemplified by a method of burning the microalga, a method of burning oil collected from the microalga, a method of burning aliphatic hydrocarbons of 16 to 26 carbon atoms, neutral lipids, and/or squalene, which have been refined from the oil collected from the microalga, or the like.

In the case of burning the microalga, it is preferable to use a dried algal biomass produced by drying the microalga so as to improve the combustion efficiency. This dried algal biomass is the same as the above-mentioned dried algal biomass according to the present invention. If the microalga is the strain JPCC DA0580, the calorific value of the dried algal biomass thereof can reach equivalent or more than the calorific value of coal (about 6000 kcal/kg).

In the case of burning oil collected from the microalga, the oil is the same as the above-mentioned oil according to the present invention. Since the oil collected from the microalga is flammable, it can be used, for example, as a fuel for a boiler or the like. If the microalga is the strain JPCC DA0580, the calorific value of the hexane extract liquid (oil) thereof can reach 8700 kcal/kg or higher.

In the case of burning aliphatic hydrocarbons of 16 to 26 carbon atoms, neutral lipids, and/or squalene, which have been refined from the oil collected from the microalga, these aliphatic hydrocarbons of 16 to 26 carbon atoms, neutral lipids, and squalene are the same as the aliphatic hydrocarbons of 16 to 26 carbon atoms, the neutral lipids, and the squalene of the above-mentioned oil according to the present invention. The aliphatic hydrocarbons of 16 to 26 carbon atoms can be used as a fuel for a diesel engine. In addition, the neutral lipids can be converted into a diesel fuel (so-called biodiesel fuel) through a known ester interchange process or the like.

<Method for Fixing Carbon Dioxide>

The method for fixing carbon dioxide of the present invention comprises a step of culturing the microalga belonging to the genus *Navicula* according to the present invention.

The photosynthesis performed by the microalga to grow has an effect to assimilate carbon dioxide of the culture solution (of the atmosphere). In other words, carbon dioxide can be fixed by culturing the microalga.

The microalga can be exemplified by the same microalgae that have been exemplified in the above-mentioned explanation of the microalga belonging to the genus *Navicula* according to the present invention.

The step of culturing the microalga is the same as the step of culturing the microalga of the above-mentioned process for producing oil according to the present invention.

Next is a more detailed explanation of the present invention with reference to Examples, although the present invention is not to be limited to these Examples.

EXAMPLE 1

Hydrocarbon Productivity of Strain JPCC DA0580

The strain JPCC DA0580 was cultured in a 24-well plate for 12 weeks, and thereafter the algal biomass was stained with Nile red, by which the production and the accumulation of oil in the algal biomass were confirmed.

Specifically speaking, the strain JPCC DA0580 was inoculated to 2 ml of the f/2 medium in a 24-well microtiter plate, and subjected to static culture under 1000 1× illumination for 12 weeks. Next, the culture solution was transferred to 1.5 ml volume microtubes and centrifuged at 13000 rpm. Then, the algal biomass was recovered as a pellet. In order to remove the medium contained in the pellet, the pellet was suspended in 0.5 ml of physiological saline and centrifuged at 13000 rpm for 5 minutes, and then the algal biomass was recovered as a pellet.

Next, this pellet was re-suspended in 450 µl of physiological saline, and 50 µl of a Nile red solution was added thereto. This suspension was mixed, and then incubated at room temperature for 10 minutes. Thereafter, this was centrifuged at 13000 rpm for 5 minutes, and then the pellet was recovered. In order to wash out the excessive Nile red solution, the pellet was suspended in 0.5 ml of physiological saline and centrifuged again, and then the algal biomass was recovered as a pellet. The yielded algal biomass was suspended in 50 µl of physiological saline and observed by fluorescence microscopy. As a result, areas with yellow fluorescent emission visualized by Nile red, indicating areas where oil resided, were found in the algal biomass. In the fluorescence microscopy image (FIG. 5), an accumulation of an abundance of oil in the form of oil droplets in the algal biomass was confirmed.

The Nile red solution refers to a solution prepared by dissolving 1 mg of Nile red in 10 ml acetone, and then diluting the dissolved product four-fold in physiological saline.

EXAMPLE 2

Identification of Hydrocarbons Accumulated in Strain JPCC DA0580

The strain JPCC DA0580 was inoculated to 500 ml of the f/2 medium in a 500 ml volume flat-shaped flask, and subjected to aeration culture at an aeration rate of 1 vvm under 3000 1× illumination for one week. Thereafter, a pellet of the algal biomass was recovered by centrifugation and lyophilized overnight.

To the yielded dried algal biomass (0.1 g) was added 6 ml of hexane, and the mixture was suspended. The extraction was carried out by disrupting the algal biomass with an ultrasonic homogenizer at room temperature for 30 minutes. Next, the hexane extract liquid was centrifuged to thereby precipitate the residue of the algal biomass. By so doing, about 6 ml of the hexane extract solution was recovered as a supernatant. To the residue of the algal biomass remaining as a precipitate was again added 6 ml of fresh hexane, and the mixture was suspended. The same extraction treatment was performed two more times (three extraction treatments in total). Thereafter, the thus recovered hexane extract liquid (about 18 ml) was introduced to a silica gel column, Sep-pak cartridge (6 cc/1 g) (manufactured by Waters Corporation), to remove neutral lipids, free fatty acids, pigments, and the like. By so doing, a 16 ml fraction of aliphatic hydrocarbons was yielded. This fraction was dried by a nitrogen gas stream, and re-dissolved with 0.5 ml of hexane. The resultant product was used as a sample. This sample was assayed by gas chromatography-mass spectrometry (GCMS) to identify hydrocarbons contained in the sample.

The gas chromatography equipment used herein was GC2010 manufactured by Shimadzu Co. The column used herein was DB-1 (column length: 30 m, column inner diameter: 0.25 mm). The assay condition was such that: the temperature was raised from 100° C. (0 min) to 330° C. (10° C./min, hold), the injection temperature was 300° C., the injection mode was splitless, the carrier gas was He, and the amount of injection was 1.0 µl.

The mass spectrometer used herein was GCMS-QP5050A manufactured by Shimadzu Co., which conducts ionization by the electron impact (EI) method.

As a result of the GCMS assay, it was revealed that the strain JPCC DA0580 had produced aliphatic hydrocarbons of 16 to 26 carbon atoms. More specifically, linear aliphatic saturated hydrocarbons of 16, 18, 20, 22, 24, and 26 carbon atoms were found as major components.

In addition, with use of a sample having 0.1% light oil dissolved in hexane as a sample for quantification, hydrocarbons produced by the strain JPCC DA0580 were quantified from the ratio of area showing the presence of these hydrocarbons in the GCMS chart. As a result, it was shown that the content percent of the linear aliphatic saturated hydrocarbons of 16, 18, 20, 22, 24, and 26 carbon atoms in the dried algal biomass of the strain JPCC DA0580 was about 0.2% by mass. This content percent was higher than the content percent of so far known algae which produce light oil-based aliphatic hydrocarbons. As described in Table 2 of Non-patent Document 1, these known algae show light oil-based aliphatic hydrocarbons accounting for 0.025 to 0.12% by mass in the dried algal biomass.

Furthermore, a peak having the largest area in the GCMS chart was identified to be of squalene. The content percent of squalene in the dried algal biomass of the strain JPCC DA0580 calculated from the peak area was about 0.3% by mass.

A trace amount of the sample, which had been taken out from the unrefined hexane extract liquid (about 18 ml) before the application to the silica gel column as described above, was also assayed by GCMS under the same condition.

As a result, it was confirmed that the hexane-extracted oil accounted for 45.5% by mass or more of the dried algal biomass of the strain JPCC DA0580. In addition, with the algal biomass of the strain JPCC DA0580 yielded from a different culture lot that had been cultured under the same condition, it was confirmed that the hexane-extracted oil accounted for 58% by mass of the dried algal biomass at its maximum.

EXAMPLE 3

Identification of Fatty Acids Constituting Triglycerides Accumulated in Strain JPCC DA0580

A pellet of the algal biomass of the strain JPCC DA0580 yielded by the same culture manner as that of Example 2 was lyophilized overnight.

About 20 ml of a hexane extract liquid was yielded in the same manner as that of Example 2, except for that 20 mg of the dried algal biomass was used as the sample and 7 ml of hexane was used per each extraction treatment. Hexane, serving as the solvent of the hexane extract liquid, was removed by evaporation with a nitrogen gas stream, thereby yielding 9.1 mg of a hexane extract product (oil). By so doing, it was confirmed that the hexane extract product (oil) accounted for 45.5% by mass of the dried algal biomass.

A 5% hydrochloric acid-methanol solution was added to the hexane extract product (oil), and the mixture was reacted in a sealed test tube at 90° C. for 2 hours, thereby causing methyl esterification of fatty acids constituting the aforementioned types of neutral lipids such as triglycerides contained in the hexane extract product. This product was then extracted by using chloroform, and the chloroform phase was taken out for use as a sample.

The sample was assayed by a GCMS device as described below. An oleic acid methyl ester was used as a reference material for quantification.

The gas chromatography device used herein was a GC6890N (model number) manufactured by Agilent Technologies International Japan, Ltd. The column used herein was a DB-WAX (column length: 30 m, column inner diameter: 0.25 mm, film thickness: 0.25 µm) manufactured by J&W. The assay condition was such that: the temperature was raised from 50° C. (0 min) to 250° C. (10° C./min, hold for 15 minutes), the injection temperature was 230° C., the injection mode was splitless injection (split ratio=10:1), the carrier gas was He (1.2 ml/min), the detector was a FID (250° C.), and the amount of injection was 0.6 µl.

The mass spectrometer used herein was JMS-GCmate-Type II manufactured by JEOL Ltd., which conducts ionization by the electron impact (EI) method.

As a result of the GCMS assay, it was found that the majority of the fatty acids constituting the aforementioned types of neutral lipids such as triglycerides were tetradecanoic acid (myristic acid (C14:0)), hexadecanoic acid (palmitic acid (C16:0)), hexadecenoic acid (palmitoleic acid (C16:1)), octadecenoic acid (oleic acid (C18:1)), and eicosapentaenoic acid (EPA (C20:5)). The contents of these fatty acids in the dried algal biomass of the strain JPCC DA0580 were, in the order of the fatty acids as set forth, about 1.0% by mass, about 12.7% by mass, about 17.0% by mass, about 0.8% by mass, and about 1.4% by mass. In other words, the fatty acids constituting the aforementioned types of neutral lipids such as triglycerides accounted for about 32.9% by mass of the dried algal biomass.

By the calculation based on the assumption that the fatty acids constituting the aforementioned types of neutral lipids such as triglycerides were all oleic acid triglycerides, it was shown that glycerin constituting the aforementioned types of neutral lipids such as triglycerides accounted for about 3.8% by mass of the dried algal biomass. In conclusion, about 36.7% by mass of the dried algal biomass was the aforementioned types of neutral lipids such as triglycerides.

EXAMPLE 4

Growth Rate of Strain JPCC DA0580

Figure 2:
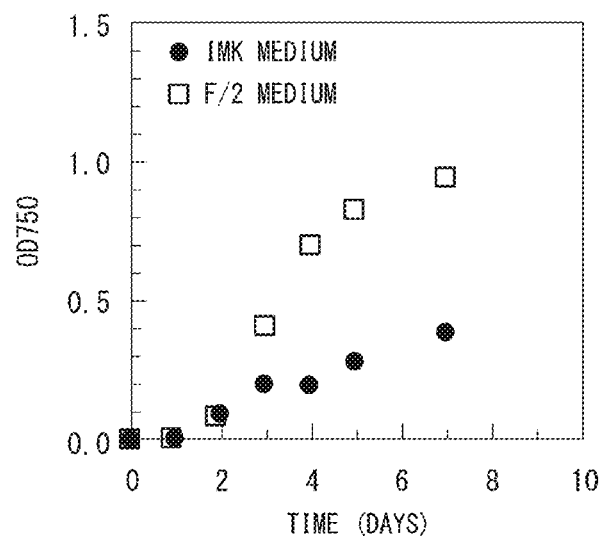
FIG. 2 shows growth curves of the strain JPCC DA0580.

The strain JPCC DA0580 was cultured in the same manner as that of Example 2. In addition, the strain JPCC DA0580 was also cultured in the same manner as that of Example 2, except for that the liquid medium was changed to an IMK medium which will be explained later. In order to evaluate the growth of the strain JPCC DA0580 in the respective media, the turbidity (OD750) of each culture solution was measured over time. The results are shown in FIG. 2.

The IMK medium was prepared in the following manner.

A liquid medium in which vitamin-including nutrient salts (200 mg/l of sodium nitrate, 1.4 mg/l of disodium hydrogen phosphate, 5.0 mg/l of sodium dihydrogen phosphate, 68 mg/l of ammonium chloride, 0.2 mg/l of thiamine, 0.0015 mg/l of biotin, 0.0015 mg/l of vitamin (B12), 37.2 mg/l of $Na_2EDTA$, 5.2 mg/l of FeEDTA, 0.3332 mg/l of MnEDTA, 0.18 mg/l of manganese (II) chloride tetrahydrate, 0.024 mg/l of zinc sulfate heptahydrate, 0.014 mg/l of cobalt (II) chloride hexahydrate, 0.0072 mg/l of sodium molybdate (VI) dihydrate, 0.0024 mg/l of copper (II) sulfate pentahydrate, and 0.0016 mg/l of selenite pentahydrate), and 37 g/l of artificial seawater (Product Name: Marine Art SF-1, manufactured by Senju Pharmaceutical Co., Ltd.) had been dissolved at the predetermined concentrations in distilled water, was prepared as the IMK medium.

From the obtained results, it was confirmed that the growth of the strain JPCC DA0580 on the f/2 medium reached OD750 of 0.05 to 0.9 in a one-week period of culture, meaning that the growth reached the plateau. The algal biomass that had reached the plateau was recovered and lyophilized. The dried algal biomass was weighed, and was 0.46 g per one liter of the culture solution.

As mentioned in Example 2 above, the content of the hexane extract product (oil) in the dried algal biomass of the strain JPCC DA0580 can reach 55% by mass or more. Thus, it was confirmed that the oil productivity of the strain JPCC DA0580 in a week reached 0.26 g or more per the culture scale of one liter.

On the other hand, the growth of the strain JPCC DA0580 on the IMK medium did not reach the plateau in a one-week period of culture.

EXAMPLE 5

Seawater Requirement of Strain JPCC DA0580

Five dilution series of nutrient liquid media were prepared by varying the concentration of the artificial seawater (Product Name: Marine Art SF-1, manufactured by Senju Pharmaceutical Co., Ltd.) in the composition of the f/2 medium that had been used in Example 2. The concentration of the artificial seawater was set at 0% when the dose was 0 g/l. Also, the concentrations were respectively set at 11.1 g/l (30%), 18.5 g/l (50%), 29.8 g/l (80%), and 37 g/l (100%).

Figure 3:
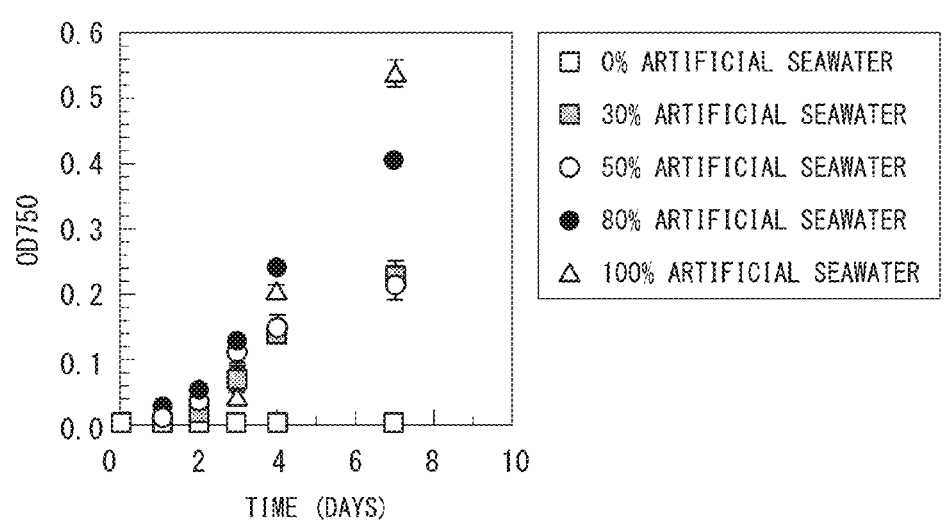
FIG. 3 shows growth curves of the strain JPCC DA0580 when cultured with variations of the concentration of seawater components.

The strain JPCC DA0580 was inoculated to 500 ml of each of these media in a 500 ml volume flat-shaped flask, and subjected to static culture for a week under the same culture condition as that of Example 2. In order to evaluate the growth, the turbidity (OD750) of each culture solution was measured over time. The results are shown in FIG. 3.

From the obtained results, it was confirmed that the growth of the strain JPCC DA0580 was best in 100% artificial seawater (seawater component) condition in a one-week period of culture. Moreover, it was also confirmed that the growth decreased along with the reduction in the concentration of the artificial seawater (seawater component), and no growth was seen in 0% artificial seawater (seawater component).

This ensured that the strain JPCC DA0580 was a marine microalga.

EXAMPLE 6

Calorific Value of Dried Algal Biomass of Strain JPCC DA0580

The strain JPCC DA0580 was cultured for a week by the same culture method as that of Example 2. Thereafter, a pellet of the algal biomass was recovered from the culture solution by centrifugation and lyophilized.

The thus yielded dried algal biomass was used as a sample. This sample was assayed by a bomb calorimeter (manufactured by Yoshida Seisakusyo Co., Ltd., model: 1013-J, calorific measurement range: 4000 to 33500 J) to measure its calorific value. This was shown to be 6730 kcal/kg. In other words, it was confirmed that the dried algal biomass of the strain JPCC DA0580 had an equivalent or higher calorific value than that of coal.

Using the thus yielded dried algal biomass as a sample, a hexane extract liquid was produced in the same manner as that of Example 2. This was dried by a nitrogen gas stream, by which a hexane extract product (oil) was produced. This was used as a sample and assayed by the bomb calorimeter to measure its calorific value. The calorific value of the hexane extract product (oil) was shown to be 8780 kcal/kg.

EXAMPLE 7

Study 1 on Organic Solvents for Extracting Oil from Algal Biomass of Strain JPCC DA0580

The strain JPCC DA0580 was cultured for a week in the same manner as that of Example 2. Thereafter, a pellet of the algal biomass was recovered from the culture solution by centrifugation.

To the pellet of the algal biomass in an undried state (0.1 g when dried) was added 6 ml of a hexane/methanol biphasic solvent (the mixture ratio (by volume) was hexane:methanol=10:1), and the mixture was suspended. The extraction was carried out by disrupting the algal biomass with an ultrasonic homogenizer at room temperature for 30 minutes. Next, the extract was centrifuged to thereby precipitate the residue of the algal biomass. By so doing, about 6 ml of the extract solution was recovered as a supernatant. To the residue of the algal biomass remaining as a precipitate was again added 6 ml of fresh biphasic solvent, and the mixture was suspended. The same extraction treatment was performed two more times (three extraction treatments in total). The thus obtained extract (18 ml in total) was dried by a nitrogen gas stream, and quantified by GCMS in the same manner as that of Example As a result, it was confirmed that the biphasic solvent-extracted oil accounted for 51.8% by mass of the dried algal biomass of the strain JPCC DA0580. The results are summarized in Table 1.

Next, a dried algal biomass (0.1 g) yielded by recovering the pellet of the algal biomass from the culture solution by centrifugation and lyophilizing it overnight, was subjected to the oil extraction in the same manner with use of a hexane monophasic solvent instead of the biphasic solvent. The thus obtained extract (18 ml in total) was dried by a nitrogen gas stream, and quantified by GCMS in the same manner as that of Example 2.

As a result, it was confirmed that the hexane monophasic solvent-extracted oil accounted for 46.2% by mass of the dried algal biomass of the strain JPCC DA0580. The results are summarized in Table 1.

In addition, the dried algal biomass (0.1 g) yielded by recovering the pellet of the algal biomass from the culture solution by centrifugation and lyophilizing it overnight, was subjected to the oil extraction in the same manner with use of the biphasic solvent (hexane/methanol (mixture ratio (by volume)=10:1)). The thus obtained extract (18 ml in total) was dried by a nitrogen gas stream, and quantified by GCMS in the same manner as that of Example 2.

As a result, it was confirmed that the hexane monophasic solvent-extracted oil accounted for 45.3% by mass of the dried algal biomass of the strain JPCC DA0580. The results are summarized in Table 1.

TABLE 1

| Alga | Undried state Biphasic solvent (% by mass) | Dried state Monophasic solvent (% by mass) | Dried state Biphasic solvent (% by mass) |
|---|---|---|---|
| Strain JPCC DA0580 | 51.8 | 46.2 | 45.3 |

In the above-mentioned results, in the oil extraction from the algal biomass of the strain JPCC DA0580 in an undried state with an organic solvent, high extraction efficiency was given by using the hexane/methanol biphasic solvent. When comparing these results, it is more preferable, in the oil extraction from the strain JPCC DA0580, to conduct the extraction by using the hexane/methanol biphasic solvent for the pellet of the algal biomass in an undried state.

EXAMPLE 8

Study 2 on Organic Solvents for Extracting Oil from Algal Biomass of Strain JPCC DA0580

The strain JPCC DA0580 was cultured for a week in the same manner as that of Example 2. Thereafter, a pellet of the algal biomass was recovered from the culture solution by centrifugation.

To the pellet of the algal biomass in an undried state (0.1 g when dried) was added 6 ml of a hexane/ethanol biphasic solvent (the mixture ratio (by volume) was hexane:ethanol=10:1), and the mixture was suspended. The extraction was carried out by disrupting the algal biomass with an ultrasonic homogenizer at room temperature for 30 minutes. Next, the extract was centrifuged to thereby precipitate the residue of the algal biomass. By so doing, about 6 ml of the extract solution was recovered as a supernatant. The thus obtained extract (6 ml in total) was dried by a nitrogen gas stream, and quantified by GCMS in the same manner as that of Example 2.

As a result, it was confirmed that the biphasic solvent-extracted oil accounted for 31.5% by mass of the dried algal biomass of the strain JPCC DA0580. The results are summarized in Table 2.

Next, a pellet of the algal biomass in an undried state (0.1 g when dried) was subjected to the oil extraction in the same manner with use of a hexane/methanol biphasic solvent (the mixture ratio (by volume) was hexane:methanol=10:1) instead of the hexane/ethanol biphasic solvent, and quantified by GCMS.

As a result, it was confirmed that the biphasic solvent-extracted oil accounted for 30.7% by mass of the dried algal biomass of the strain JPCC DA0580. The results are summarized in Table 2.

Note that the reason why the oil extraction yield in Example 8 was smaller than the oil extraction yield in Example 7 is that the number of times of extraction with the organic solvent was reduced from three times (Example 7) to once (Example 8).

TABLE 2

| Alga | Undried state Biphasic solvent (% by mass) Hexane/methanol | Undried state Biphasic solvent (% by mass) Hexane/ethanol |
|---|---|---|
| Strain JPCC DA0580 | 30.7 | 31.5 |

Oil Extraction Efficiency from Biomass of Microalga Belonging to Different Genus Three types of microalgae, *Scenedesmus* (*Scenedesmus rubescens* strain JPCC GA0024, Accession number: FERM P-21749), cyanobacteria (*Synechocystis* sp.), and *Tetraselmis* (*Tetraselmis striata*), were cultured by known methods, respectively yielding the pellets of the algal biomass. These three types of microalgae have properties to accumulate oil in their algal biomass. The oil includes at least neutral lipids such as triglycerides.

A pellet of each algal biomass in an undried state (0.1 g when dried) was used as a sample, which was subjected to the oil extraction with use of a biphasic solvent (hexane/methanol (mixture ratio (by volume)=10:1)) in the same manner as that of Example 7.

Next, a pellet of each algal biomass in a dried state (0.1 g) was used as a sample, which was subjected to the oil extraction with use of a monophasic solvent (hexane) in the same manner as that of Example 7.

In addition, the pellet of each algal biomass in a dried state (0.1 g) was also used as a sample, which was subjected to the oil extraction with use of a biphasic solvent (hexane/methanol (mixture ratio (by volume)=10:1)) in the same manner as that of Example 7.

The thus obtained extract (18 ml in total) was dried by a nitrogen gas stream, and quantified by GCMS in the same manner as that of Example 2. The results are summarized in Table 3.

TABLE 3

| Alga | Undried state Biphasic solvent (% by mass) | Dried state Monophasic solvent (% by mass) | Dried state Biphasic solvent (% by mass) |
|---|---|---|---|
| Scenedesmus | 6.7 | 22.7 | 4.9 |
| Cyano-bacteria | 4.0 | 12.9 | 5.4 |
| Tetraselmis | 3.0 | 19.4 | 10.1 |

From the results of Table 3, it is apparent that, when it comes to the oil extraction from the algal biomass of known microalgae by using an organic solvent, the oil extraction yield from the algal biomass in an undried state is remarkably low. In other words, a step of previously drying the algal biomass is a must. No small amount of time and cost are necessary for the process of drying the algal biomass.

On the other hand, the algal biomass of the microalga according to the present invention has quite excellent properties that enable efficient extraction of oil from the algal biomass in an undried state. Therefore, it is possible to reduce the energy for the production process of a biofuel or the like from the microalga of the present invention.

INDUSTRIAL APPLICABILITY

The microalgae according to the present invention have high ability to produce aliphatic hydrocarbons of 16 to 26 carbon atoms, and thus are applicable to the production of a diesel fuel, which shows promise as a carbon neutral fuel intended for the prevention against global warming. The strain JPCC DA0580 of the present invention shows particular promise because it is highly capable of producing neutral lipids and squalene, as well as being capable of producing aliphatic hydrocarbons of 16 to 26 carbon atoms as mentioned above.

The neutral lipids can be converted into a diesel fuel (so-called biodiesel fuel) through a known ester interchange process or the like.

The invention claimed is:

1. An isolated microalga, *Navicula oiliticus* strain JPCC DA0580 (FERM BP-11201).

2. A process for producing oil, comprising culturing the microalga according to claim 1 in a medium.

3. The process for producing oil according to claim 2, further comprising culturing the microalga with a different medium having lower concentration(s) of nutrient salt(s).

4. The process for producing oil according to claim 2, wherein said oil includes a neutral lipid.

5. The process for producing oil according to claim 2, wherein said oil includes squalene.

6. The process for producing oil according to claim 2, further comprising extracting oil from the culture product with an organic solvent selected from the group consisting of n-hexane, a solvent comprising n-hexane and methanol, and a solvent comprising n-hexane and ethanol.

7. A dried algal biomass comprising the microalga according to claim 1.

8. A method for fixing carbon dioxide, comprising culturing the microalga according to claim 1.

* * * * *

UNITED STATES PATENT AND TRADEMARK OFFICE
CERTIFICATE OF CORRECTION

PATENT NO. : 8,927,285 B2
APPLICATION NO. : 13/263005
DATED : January 6, 2015
INVENTOR(S) : Mitsufumi Matsumoto Page 1 of 2

It is certified that error appears in the above-identified patent and that said Letters Patent is hereby corrected as shown below:

Title page

Page 1 (item 75 – inventor), line 1, "Kitakyusyu (JP)" should be --Kitakyushu (JP)--.

Page 1 (item 56), col. 2, line 16, under Other Publications, "Phycologhgy," should be --Phycology,--.

Specification

Col. 3, line 17, "phylogenic" should be --phylogenetic--.

Col. 4, line 34, "(1x)" should be --(lx)--.

Col. 6, lines 4-10, "The strain JPCC DA0580 was deposited.....Mar, 16, 2009)."
should be --The strain JPCC DA0580 was deposited with the International Patent Organism Depositary, National Institute of Advanced Industrial Science and Technology on Dec. 4, 2009 with the accession number of FERM BP-11201. The depository is located at AIST Tsukuba Central 6, 1-1, Higashi 1-chome Tsukuba-shi, Ibaraki-ken 305-8566, Japan. The AIST deposit was accompanied by documents describing scientific characteristics and taxonomic position and thus meets all of the requirements of the Budapest treaty. The specific biological materials will be irrevocable and without restriction or condition released to the public upon the issuance of patent.--.

Col. 6, lines 11-22, "The strain JPCC DA0580 was deposited.....issuance of patent."
should be --The strain JPCC DA0580 is capable of accumulating oil including aliphatic hydrocarbons of 16 to 26 carbon atoms, neutral lipids, and squalene, in the algal biomass. Furthermore, the content percent of the aliphatic hydrocarbons of 16 to 26 carbon atoms in the dried algal biomass of the strain JPCC DA0580 can reach 0.2% by mass or more. Moreover, the content percent of the neutral lipids in the dried algal biomass of the strain JPCC DA0580 can reach 36% by mass or more. In addition, the content percent of the squalene in the dried algal biomass of the strain JPCC DA0580 can reach 0.3% by mass or more.--.

Signed and Sealed this
Thirteenth Day of October, 2015

Michelle K. Lee
*Director of the United States Patent and Trademark Office*

CERTIFICATE OF CORRECTION (continued)
U.S. Pat. No. 8,927,285 B2

Col. 7, lines 66-67; col. 8, lines 1-2; col. 12, line 49; and col. 13, line 17, "1x" should be --lx--.

Col. 17, line 4, "Example" should be --Example.--.

Claims

Col. 22, line 16 (claim 6), "solvent" should be --solvent,--.

SEQUENCE LISTING

```
<160> NUMBER OF SEQ ID NOS: 1

<210> SEQ ID NO 1
<211> LENGTH: 1641
<212> TYPE: DNA
<213> ORGANISM: Navicula

<400> SEQUENCE: 1
actttgaaac tgcgaacggc tcattatatc agttatagtt tatttgatag tcccttacta      60
ctcggataac cgtagtaatt ctagagctaa tacgtgcgtc aatactcttc ggagtagtat     120
ttattagatg gaaaccaact gcttcggcat gatgtggtga ttcataataa gcttgcggat     180
cgcgtgcttc ggcygcgatg gatcattcaa gtttctgccc tatcagcttt gacggtactg     240
tattggagta ccgtggcggt aacgggtaac gggaaattag ggtttgacac cggagaggga     300
gcctgagaga cggctaccac atccaaggaa ggcagcaggc gcgtaaatta cccaatcttg     360
acacaaggag gtagtgacaa taaataacaa tgccgggcct ttctaggtct ggcaattgga     420
atgagaacaa tttaaacccc ttatcgagga tccattggag ggcaagtctg gtgccagcag     480
ccgcggtaat tccagctcca atagcgtata ttaaagttgt tgcagttaaa aagctcgtag     540
ttggatttgt ggcgtgcgtt gcggcgtcca ttgatttggt tctgcctyga ccgcgccatc     600
cttgggtgga atctgygtgg cattaggttg tcgtgcaggg gatgcccatc gtttactgtg     660
aaaaaattag agtgttcaaa gcaggcttat gccgttgaat atattagcat ggaataataa     720
gataggtcta gggtcctatt ttgttggttt gcggtccttg gaaatgatta acagggacag     780
ttgggggtat tcgtattcca ttgtcagagg tgaaattctt ggatttctgg aagacgaact     840
actgcgaaag catttaccaa ggatgttttc attaatcaag aacgaaagtt aggggatcga     900
agatgattag ataccatcgt agtcttaacc ataaactatg ccgacaaggg attggcgggg     960
ttcgtttcgt ctccgtcagc accttatgag aaatcacaag ttttggggtt ccggggggag    1020
tatggtcgca aggctgaaac ttaaagaaat tgacggaagg gcaccaccag gagtggagcc    1080
tgcggcttaa tttgactcaa cacgggaaaa cttaccaggt ccagacatag tgaggattga    1140
cagattgaga gctctttctt gattctatgg gtggtggtgc atggccgttc ttagttggtg    1200
gagtgatttg tctggttaat tccgttaacg aacgagaccc ctgcctgcta aatagtcccg    1260
cgagtgaatt tcactggcgc ggtcttctta gagggacgtg cgttctattm gacgcaggaa    1320
```

```
gataggggca ataacaggtc tgtgatgccc ttagatgttc tgggccgcac gcgcgctaca    1380
ctgatgcatt caacgagtgt tyttccttgg ccgagaggcc tgggcaatct tttgaacgtg    1440
catcgtgata gggatagatt attgcaatta ttaatcttga acgaggaatt cctagtaaac    1500
gcagatcatc aatctgcatt gattacgtcc ctgccctttg tacacaccgc ccgtcgcacc    1560
taccgattga atggtccggt gaagcctcgg gattgtggct gttgccttyr cgggtggcgg    1620
ttgcgagaac ttgtctaaac c                                              1641
```